United States Patent
Fu et al.

(10) Patent No.: US 10,238,676 B2
(45) Date of Patent: Mar. 26, 2019

(54) APPLICATION OF GINSENOSIDE RG3 IN PREPARING MEDICINE FOR PREVENTING AND/OR TREATING DEMENTIA, AND MEDICINE FOR TREATING DEMENTIA

(71) Applicant: Li Fu, Dalian (CN)

(72) Inventors: Li Fu, Dalian (CN); Kaiqian Wang, Dalian (CN); Qiang Fu, Dalian (CN); Zhengxian Liu, Dalian (CN); Qi Lu, Dalian (CN); Xin Gai, Dalian (CN)

(73) Assignee: Li Fu, Dalian (CN)

( * ) Notice: Subject to any disclaimer, the term of this patent is extended or adjusted under 35 U.S.C. 154(b) by 234 days.

(21) Appl. No.: 15/036,494

(22) PCT Filed: Nov. 6, 2014

(86) PCT No.: PCT/CN2014/090475
§ 371 (c)(1),
(2) Date: May 13, 2016

(87) PCT Pub. No.: WO2015/074494
PCT Pub. Date: May 28, 2015

(65) Prior Publication Data
US 2016/0271154 A1  Sep. 22, 2016

(30) Foreign Application Priority Data
Nov. 22, 2013 (CN) .......................... 2013 1 0589909

(51) Int. Cl.
| A61K 31/704 | (2006.01) |
| A61K 36/888 | (2006.01) |
| A61K 36/9066 | (2006.01) |
| A61K 36/236 | (2006.01) |
| A61K 36/258 | (2006.01) |
| A61K 36/42 | (2006.01) |

(52) U.S. Cl.
CPC .......... *A61K 31/704* (2013.01); *A61K 36/236* (2013.01); *A61K 36/258* (2013.01); *A61K 36/42* (2013.01); *A61K 36/888* (2013.01); *A61K 36/9066* (2013.01)

(58) Field of Classification Search
CPC .... A61K 31/704; A61K 36/42; A61K 36/236; A61K 36/258; A61K 36/888; A61K 36/9066; A61K 2300/00

USPC ........................................................ 514/26
See application file for complete search history.

(56) References Cited

U.S. PATENT DOCUMENTS

| 9,333,215 | B2 * | 5/2016 | Fu ........................ A61K 9/0019 |
| 2005/0245465 | A1 * | 11/2005 | Kim ....................... C07H 15/24 |
| | | | 514/26 |

FOREIGN PATENT DOCUMENTS

| CN | 101031580 | 9/2007 |
| CN | 101133075 | 2/2008 |
| CN | 101312650 | 11/2008 |

OTHER PUBLICATIONS

The Merck Manual, 16th Edn. 1992, pp. 1403-1407.*
Yang et al, J. Pharmacy and Pharmacology, 2009, 61, 375-380.*
Liu et al, Journal of Traditional Chinese Medicine, Aug. 15, 2013, 33(4), 449-454.*
International Search Report for International application No. PCT/CN2014/090415, dated Feb. 2, 2015.
Wang, R., "Neuroprotective Effects and Brain Transport of Ginsenoside Rg1", ScienceDirect, Chinese Journal of Natural Medicines, 2009, pp. 315-320, vol. 7, No. 4.
Hou, J. "Ginsenoside Rg3 Prevents Oxidative Stress-Induced Astrocytic Senescence and Ameliorates Senescence Paracrine Effects on Glioblastoma", Molecules, 2017, pp. 1-14, 22, 1516.

* cited by examiner

*Primary Examiner* — Ganapathy Krishnan
(74) *Attorney, Agent, or Firm* — Greer, Burns & Crain, Ltd.

(57) ABSTRACT

The present invention discloses an application of ginsenoside Rg3 in preparing a medicine or product for preventing and treating dementia, and a preparation method thereof, which belong to the fields of medicines and health care products, and its products comprise a topical preparation, oral preparation and injection of the ginsenoside Rg3; and the Rg3 medicine or formulating prepared Rg3 compound medicine is prepared by using a solubilizer, a transdermal agent, a reagent promoting the absorption by penetrating a blood-brain barrier and an extractive, achieving the effect that the medicine penetrates the blood-brain barrier, and is used for preventing and treating dementia.

3 Claims, 2 Drawing Sheets

APPLICATION OF GINSENOSIDE RG3 IN PREPARING MEDICINE FOR PREVENTING AND/OR TREATING DEMENTIA, AND MEDICINE FOR TREATING DEMENTIA

This application is a U.S. National Phase under 35 U.S.C. § 371 of International Application No. PCT/CN2014/090475, filed Nov. 6, 2014, which claims priority under 35 U.S.C. §§ 119 and 365 to Chinese Application No. 201310589909.0, filed Nov. 22, 2013.

TECHNICAL FIELD

The present invention relates to a ginsenoside Rg3 pharmaceutic preparation and a preparation method and application thereof, which belong to the field of medicines.

BACKGROUND ART

When entering the $21^{st}$ century, with the aging of the population, the morbidity of senile dementia is increasing year by year in the world. There are about 20 million people suffering from senile dementia around the world as reported, wherein there are about 5-7 million people in China. The number of people who died because of suffering from senile dementia is in the fourth place after heart disease, cancer and stroke. In China, the morbidity of dementia of people over 65 years old is 6-7%; the morbidity of dementia of people over 70 years old is 13-15%; the morbidity of dementia of people over 80 years old is 22-25%; unfortunately, there are no better methods to effectively treat and prevent the senile dementia.

The senile dementia comprises Alzheimer's disease (AD) and vascular dementia (VD), the modern medical science has not figured out the pathogenesis of AD, and it is currently considered to be a progressive and neuro-degenerative disease. However, the VD is various dementias resulted from neurocranium internal hemorrhage, multiple infarct, arteriosclerosis encephalopathy acute brain trauma, encephalic space-occupying lesion, alcoholic intoxication, brain nutritional deficiency and metabolic endocrine disorder.

No matter what results in the senile dementia, the early symptoms are all forgetfulness, and hypesthesia of computational power and language competence; the second phase is serious memory loss, direction loss and of few words; and the third phase is serious thinking capacity disorder and vague orientation. Therefore, for studying the prevention and treatment of the senile dementia, it is prime to prevent memory and intelligence decline, and the ginsenoside Rg3 has significant effects of improving memory and delaying the ageing, which is also one of objectives of the present invention.

At present, a large number of medical research materials prove that the cerebral cortex and hippocampal cholinergic neurons of people suffering from senile dementia are largely lost, the presynaptic specific cholinergic mark choline acetyl transferase (ChAT) of a cholinergic transfer medium acetyl choline (Ach) is remarkably decreased, and this is one of disease causes of the senile dementia, so how to increase the functions of a reticular formation ascending activating system of the brain stem and promote Ach synthesis is an effective method for preventing and treating the senile dementia. Ginsenoside Rg3 can effectively activate the functions of the reticular formation ascending activating system of the brain stem, promote the Ach synthesis, increase cerebral blood flow, improve microcirculation, and therefore can be used for preventing and treating the senile dementia, and this is also the second objective of the present invention.

At present, the medicines used for preventing and treating the dementia mainly include donepezil, rivastigmine, galantamine, piracetam, aniracetam, vinpocetine, nicergoline, dihydroergotoxine, huperaine A, ginkgo leaves agent, brain protein hydrolysate, citicoline, cholinesterase inhibitor, xanthine, nonsteroidal anti-inflammatory medicine, estrogen, etc. Although these medicines have a certain relieving effect, but side effects are great, limiting their general use.

Chinese medicines for treatment of senile dementia are as follows: firstly, on the aspect of treatment from the standpoint of liver and kidney, body essence and marrow supplementing prescriptions are mostly adopted, such as Radix Rehmanniae Preparata, Fructus Corni, Rhizoma Polygonati, Carapax et *Plastrum Testudinis*, Colla Corii Asini, Fructus Lycii, Cornu Cervi Pantotrichu, etc; secondly, on the aspect of treatment through phlegm, the prescriptions for invigorating spleen to eliminate dampness, eliminating phlegm, inducing resuscitation and restoring consciousness are mostly adopted, such as Radix Curcumae, Rhizoma Acori Tatarinowii, Radix Polygalae, Fructus Alpiniae Oxyphyllae, XINGSHEN JIAONANG and the like;

thirdly, on the aspect of treatment through QI-stagnation and blood stasis, the prescriptions for regulating QI, activating blood circulation, inducing resuscitation and restoring consciousness are mostly adopted, such as DANGGUI-SHAOYAO SAN, BUYANGHUANWU TANG, TONGMAIYIZHI DAN and the like.

However, these Chinese medicines needs to be administered by a herbalist doctor based on differential treatment that varies from person to person, and cannot be used by the patients alone as they are incapable of taking these Chinese medicines properly. The effective ingredient ginsenoside Rg3 extracted from natural plants of the present invention have high purity (80% or above 80%) and is unique in curative effect, a prepared preparation is convenient to use, patients can adjust the dosages according to self reactions by themselves, and the effect of the ginsenoside after transdermal absorption is moderate and lasting.

*Panax ginseng* C. A. Mey. is an araliaceae perennial herb and is regarded as the top grade and described as that the Radix Ginseng mainly reinforces internal organs, soothes mind and body tranquilization, calms spirits, relieves palpitation due to fear, improves eyesight, is uplifting, is beneficial to intelligence and has the effects of reducing body weight and prolonging life after being taken for a long time in the Chinese pharmaceutical ancient book in regard to traditional Chinese medicine <Shen Nong's Herbal Classic>. Modern medical research and chemical laboratory analysis show that a chemical substance named as ginsenoside is contained in the Radix Ginseng and has the obvious effects of regulating the central nervous system of human, strengthening heart, resisting fatigue, regulating substance metabolism and the like, and therefore a good therapeutic effect is played on the multiple diseases of the nervous system, the cardiovascular system, the endocrine system and reproductive system.

The Radix Ginseng can regulate the balance of the excitation process and inhibition process of the central nervous system. The results of research of the influence on brain electrical activities of animals of the Radix Ginseng show that: the Radix Ginseng influences the two nerve processes of excitation and inhibition, but mainly strengthen the excitation process of the cerebral cortex. Due to the fact that the ginseng acts on the inhibition process at the same time, the inhibition tends to concentration, and differentiation is accelerated and is more complete. The Radix Ginseng can regulate nerve functions and enable the disordered nerve process caused by tension to be restored.

Some reports suggest that Radix Ginseng extract has an antagonism effect on poor memory caused by anisodine and pentobarbital sodium, can also improve memory consolidation impairment caused by cycloheximide and sodium nitrite and memory reappearance deficits caused by 40% ethyl alcohol. Radix Ginseng stem-leaf saponins are injected into the abdominal cavity of rats in dosages of 200 mg/kg, 100 mg/kg and 50 mg/kg, the anisodine effect can be obviously resisted, the memory of the rats can be obviously improved, intracerebral RNA can be obviously increased, but no obvious effect is produced on the DNA and protein content.

The Radix Ginseng also has obvious impact on cerebral blood flow and cerebral energy metabolism. A Radix Ginseng preparation can improve glucose intake of the rabbit brain, at the same time, reduces the ratio of lactic acid, pyruvic acid and lactic acid/pyruvic acid, and makes the utilization of glucose to transfer to aerobic metabolism from an anaerobic metabolism pathway. The Radix Ginseng also can make free inorganic phosphorus in the cerebral cortex increase by 25%. The Radix Ginseng fruit saponin can improve oxygen uptake ability of the brain. The total Radix Ginseng saponin and total Radix Ginseng root saponin both have protection against cerebral ischemia/reperfusion injury. In sum, the Radix Ginseng can make animal brains more reasonably utilize energy substance glucose, generates energy with oxidation, and synthesizes more ATP for activity use such as learning, memorizing and the like.

The ginsenoside Rg3 is a Radix Ginseng rare saponin, which is only contained in radix *ginseng rubra* over more than 5 years for 3 parts per 10 million, and is the most essential component in the Radix Ginseng. The ginsenoside Rg3 has improving and preventing effects on various diseases, and has a great therapeutic effect on elderly common diseases, such as cardiovascular and cerebrovascular diseases, coronary heart disease, limbs acratia, disability, memory impairment.

The ginsenoside Rg3 is Radix Ginseng glycol tetracyclic triterpenoid saponin, it is found in practical applications that since the ginsenoside Rg3 has a larger molecular weight (785.02), its lipid solubility and water solubility are both relatively poor, making its oral absorption percentage being about 10.28%, and resulting in relatively poor absorption of oral preparations, results of animal pharmacokinetic experiments indicate that about 80% of the medicine in native form is not absorbed and is excreted through feces, and the medicine is not fully used in the body, which will influence full use of its clinical therapeutic effect. Therefore, the ginsenoside Rg3 is made into topical preparations, which directly enters the lymphatic system by absorption via neck skin and posterior auricular mucosa, it is absorbed via the blood-brain barrier so as to achieve a therapeutic effect on the cerebral nervous system, and a better clinical therapeutic effect is obtained and further confirmed through pharmacological experiments and clinical applications.

Borneolum Syntheticum: studies of immunohistochemical staining technique adopted by Zhao Baosheng, et al. show that Borneolum Syntheticum can not induce expression of ICAM-1 on rat brain microvascular EC, but can significantly reduce adhesion of leukocytes and EC during brain trauma, and has a protective effect on EC, the studies prove that the promotion of openness of the blood-brain barrier with borneolum syntheticum is irrelevant to ICAM-1, and borneolum syntheticum has a certain protective effect on the rat brain tissue with brain trauma. Rats are divided into 12 groups by Ge Chaoli, et al., drenched with a borneolum syntheticum paraffin oil solution 10, 13 mL·kg, and are also divided into 1, 2, 4, 8, 24, 48 hours for each group according to the difference of sampling time points, the control group is drenched with equal amount of paraffin oil solution. The two groups of rats are sacrificed and brains are taken at above-mentioned time points, respectively, and observed with a transmission electron microscope. The studies show that borneolum syntheticum has a significant influence on tight junction between rat cerebral capillary endothelial cells; compared with the control group, intercellular tight junction gaps are widened, are discontinous, and are reduced in structure, after drench with borneolum syntheticum for 4 hours, changes start to occur, reach to peak at the $8^{th}$ hour, and return to normal at the $48^{th}$ hour, which indicates that borneolum syntheticum can make ultra microstructures of the rat blood-brain barrier have reversible changes. The rabbit serum containing traditional Chinese medicine borneolum syntheticum prepared by Chen Yanming uses verapamil as positive control medicine, it is observed and found with an MTT method that on MDCK (Madin-Darby Canine Kidney) and HeLa (human uterine cancer) cell lines, borneolum syntheticum can both significantly increase cell toxicity caused by vincristine, and has a similar effect with verapamil, which illustrates that borneolum syntheticum has a significant inhibition effect on expression of P-glycoprotein. There are also studies which show that promotion of physiological openness of the blood-brain barrier with borneolum syntheticum is due to the fact that after borneolum syntheticum enters the blood-brain barrier, affinity of borneolum syntheticum with P-glycoprotein is large, as a result, the borneolum syntheticum is pumped out of cells, thus the vascular active substance 5-HT which has small affinity with P-glycoprotein is accumulated in cells so as to promote openness of the blood-brain barrier.

*Styrax*: rats are divided into a sulpiride combined storax group and a single-use sulpiride group, after the rats continuously take oral medication for one week, the surgery for installing probes in the brain and neck of rats are performed, the equilibration is waited for one hour, dialysate in the blood of right atrium of rats and dialysate in intracerebral hippocampal tissues are collected at each time period (30, 60, 90, 120, 150, 180 minutes) by blood microdialysis and brain microdialysis methods, respectively, the content of sulpiride in the sample is detected by a reversed-phase high-performance liquid fluorescence chromatogram system, and the content of sulpiride in the brain and the blood are compared after medicine administration by a statistic method. As a result, it is obvious that the concentrations of sulpiride in the brain and blood of rats in the sulpiride combined storax group are higher than that in the single-use sulpiride group, the concentration ratio of sulpiride in the blood and brain of rats is 1:0.2 in the single-use sulpiride group, the concentration ratio of sulpiride in the blood and brain of rats is raised to 1:0.3 in the sulpiride combined storax group, and compared with the single-use sulpiride group, the concentration of sulpiride in the brain is raised by 39% and the concentration of sulpiride in the blood is raised by 69% in the sulpiride combined storax group. This indicates that the storax can significantly increase the concentrations of sulpiride in the brain and blood of rats, and the storax can facilitate the sulpiride to penetrate the gastrointestinal barrier and the blood-brain barrier.

Moschus: expert experiments indicate that: a Moschus aqueous solution or suspension which is used for intravenous injection by 50 mg/kg or for lateral ventricle injection by 2.5 mg/kg can de-synchronize the quiet and awake rabbit cortex electroencephalogram (EEG) for a short time, and part of animals are with restlessness behavior in a watch state, indicating that the cerebral cortex can be excited and the cortical electrical activity can be enhanced; the Moschus aqueous solution has an obvious wake-up effect on anesthetized rabbits, lateral ventricle injection is more effective than intravenous injection, and the above specification may describe that the Moschus likely penetrates the blood-brain barrier to directly act on the central nervous system.

Rhizoma Acori Tatarinowii: rhizoma acori tatarinowii is one of traditional resuscitation-inducing aromatic herbs, is singly used among the people or is compatible with other traditional Chinese medicines for wide usage, is mainly used for treating encephalopathy and has a definite curative effect, and it prompted that the rhizoma acori tatarinowii has a certain effect on the BBB. Volatile oil is extracted by adopting the volatile oil extraction method I described in the appendix I of the Chinese Pharmacopoeia 2005, the extraction rate is about 1.58%, and an oil removing water decoction is concentrated to be 1 g/ml. A gas chromatography-mass spectrometer (GC/MS) is adopted to detect that a volatile oil sample contains α-asarone, β-asarone, guaiene and acorenone, the cerebrospinal fluid of a rat taking the volatile oil is detected under the same conditions, and a result shows that the α-asarone and the β-asarone can penetrate the BBB to enter the cerebrospinal fluid. A liquid chromatography-mass spectrometer (HPLC/MS) is adopted to determine an oil removing water decoction sample and the cerebrospinal fluid sample of a rat drenched with the oil removing water decoction, three compounds are detected, the molecular weights are 396, 452 and 339 respectively, and a known rhizoma acori tatarinowii compound is not yet included therein. The ultra microstructures of the cerebral cortex BBB of the rats before and after medicine administration are observed through the transmission electron microscope, it can be found that all extracted parts of the rhizoma acori tatarinowii enable the tight junction (TJ) of BBB endothelial cells to be loose, but the BBB is basically complete and is not yet destroyed. Borneolum syntheticum is used as a positive medicine to preliminarily discuss the promoting effect on BBB passage of Evans blue (EB) of the extracted parts of the rhizoma acori tatarinowii, namely the EB content in the brain reflects the permeability of the BBB, the statistical analysis shows that the EB content in the brain is remarkably higher than that of a blank group (P<0.01) 2.5 hours after the borneolum syntheticum is filled into the stomach, and the self-administrating medicine with the rhizoma acori tatarinowii dose of 11.7 g/kg does not produce an obvious effect within 0.5 to 2.5 hours; the administration time of the rhizoma acori tatarinowii is prolonged, the EB content in the brain after 5 hours is remarkably higher than that of the blank group (P<0.05) when the volatile oil doses of the rhizoma acori tatarinowii are 23.4 g/kg and 11.7 g/kg, and a dose dependency trend exists; when the total dose is 11.7 g/kg, the EB content in the brain after 5 hours is remarkably higher than that of the blank group (P<0.01). One week after the extracted parts of the rhizoma acori tatarinowii are filled into the stomachs of the rats, phenytoin sodium is injected into the abdominal cavity, an HPLC method is adopted to detect the concentration of the phenytoin sodium in the brain, and a result shows that: the content of the phenytoin sodium in the brain of the total-group animal taking the rhizoma acori tatarinowii is higher than that in the brain of the animal group which does not take the rhizoma acori tatarinowii, but a higher concentration (P<0.01) is still kept after 4 hours. An HPLC-ECD is utilized to detect the concentration of 5-hydroxytryptamine (5-HT) in brain tissues, and statistical analysis shows that: compared with the blank group, the content of the 5-HT in the brain of the rat in the volatile oil group is increased (P<0.05) and the content of the 5-HT in the rhizoma acori tatarinowii water decoction group and the content of 5-HT in the total medicine group are remarkably increased (P<0.01). A HeLa cell line is applied to serve as a carrier for evaluating the activity of the rhizoma acori tatarinowii to P-glycoprotein on the BBB, and the parts (volatile oil, water decoction and total medicine) of the rhizoma acori tatarinowii can obviously strengthen the cytotoxicity of vincristine (VCR) after 0.5 hour (P<0.01); the volatile oil part can still obviously strengthen the cytotoxicity of the VCR after 8 hours (P<0.01), and the medicine effect maintaining time of the volatile oil is obviously longer than that of the positive medicine verapamil (VER) (P<0.01); the positive medicine and the parts of the rhizoma acori tatarinowii have no obvious effect on the cytotoxicity of the VCR after 24 hours (P>0.05). In sum, the rhizoma acori tatarinowii can affect the ultra microstructure of the rat BBB, strengthen the permeability of the BBB to the EB and promote increase of the content of the CNS medicine phenytoin sodium entering the brain and has the pharmacological actions of activating the BBB and leading medicines to the brain. Action mechanism research results show that the 5-HT content regulation by the rhizoma acori tatarinowii is one of its BBB permeability increase mechanisms, and in addition, the rhizoma acori tatarinowii has a very strong effect of inhibiting exocytosis of the P-glycoprotein medicine on the HeLa cell membranes, which is also an action mechanism of BBB permeability increase.

Radix Curcumae: the curcumin contained in the Radix Curcumae has an effect of inhibiting the senile dementia. The main cause of the dementia is intertwining of amyloid β. The curcumin enables the intertwined amyloid β to be loosened. The curcumin is a powerful antioxidant and anti-inflammatory chemical molecule and can penetrate the strictly guarded blood-brain barrier to neutralize oxides and copper ions having oxidative toxicity, and beyond that, the curcumin can further inhibit a cell transcription factor (NF kappa B) causing inflammation. Therefore, the curcumin is a key ingredient for protecting the brain tissues and decreasing dementia. In India, the number of patients with dementia is only ten percent of those in other countries, and curcumin's contributions cannot go unnoticed.

CONTENTS OF THE INVENTION

The primary objective of the present invention is to provide the performance and effect of 20(R)-ginsenoside Rg3 in preventing or/and treating dementia and to provide new pharmaceutical uses of 20(R)-ginsenoside Rg3, namely new applications in medicines or health foods for treating, coordinating and relieving dementia.

Another objective of the present invention is to provide a ginsenoside Rg3 topical preparation for clinical use defects of ginsenoside Rg3 such as poor oral absorption and poor blood-brain barrier penetration. The ginsenoside Rg3 topical medicinal preparation of the present invention is applied directly on both sides of the nose, a neck and the skin behind ears, for treating dementia, particularly treating and preventing Alzheimer's disease.

To achieve the purpose, on one hand, the invention provides applications of 20(R)-ginsenoside Rg3 in preparing a medicine or health care product for preventing or/and treating dementia, wherein the dementia is Alzheimer's disease and vascular dementia, preferably Alzheimer's disease, and wherein the medicine is composed of 20(R)-ginsenoside Rg3 and a pharmaceutically acceptable carrier.

Particularly, the medicine further comprises one or more of Radix Ginseng oil, Rhizoma Chuanxiong oil, Rhizoma Acori Tatarinowii oil, Moschus oil or Radix Curcumae oil.

The 20(R)-ginsenoside Rg3 of the present invention can be used to prevent or treat dementia either alone or in the form of a medicinal composition containing the 20(R)-ginsenoside Rg3.

The medicine of the invention is administered by oral, sublingual, transdermal, intramuscular, subcutaneous, mucocutaneous and intravenous ways.

The present invention provides a medicinal preparation for preventing or treating dementia, with 20(R)-ginsenoside Rg3 used as an active component, and corresponding pharmaceutical dosage forms. The medicinal preparation uses the 20(R)-ginsenoside Rg3 as an active component and comprises other pharmaceutically acceptable carrier components, wherein the content of 20(R)-ginsenoside Rg3 is equal to or greater than 80%, preferably higher than 90%, and further preferably higher than 95%.

The medicine of the present invention is present in forms of oral preparation, injection and topical preparation. Wherein the oral preparation comprises tablets, capsules, pills, powder, granules, syrups or solutions; the injection comprises an injectable solution or lyophilized powder for injection; and the topical preparation comprises cream, ointments, sprays, aerosols, patches, gels, naristillaes or cataplasms.

The medicine of the present invention is present in forms of tablets, capsules, pills, powder, granules, syrups, solutions, injections, sprays, aerosols, patches, gels, naristillaes or cataplasms, namely medicinal preparations comprise tablets, capsules, pills, powder, granules, syrups, solutions, injections, sprays, aerosols, patches, gels, naristillaes, cataplasms and the like, but are not limited to the forms above.

On the other hand, the present invention provides a medicine or health care product containing 20(R)-ginsenoside Rg3 for preventing or/and treating dementia.

Wherein the medicine or health care product further comprises one of Radix Ginseng volatile oil, Moschus volatile oil, Rhizoma Acori Tatarinowii volatile oil, Radix Curcumae volatile oil or Rhizoma Chuanxiong volatile oil.

Particularly, the content of the 20(R)-ginsenoside Rg3 in the medicine or health care product is ≥80%, preferably higher than 90%, and further preferably higher than 95%.

The inventor employed advanced separation and purification techniques to extract active component 20(R)-ginsenoside Rg3 for preventing and treating dementia from medicinal Radix Ginseng through considerable modern scientific research and carried out anti-dementia pharmacodynamical and pharmacological studies on the 20(R)-ginsenoside Rg3 and its corresponding medicinal preparations, results show that monomers of the 20(R)-ginsenoside Rg3 provide a clear pharmacological action, high anti-dementia efficacy, a low toxic or side effect and high safety, and a highly effective and low toxic medicine is provided for anti-age and anti-dementia.

Compared with existing medicines for preventing and treating dementia, the present invention has the following advantages:

1. The present invention explores new medicinal value of the known compound 20(R)-ginsenoside Rg3, the 20(R)-ginsenoside Rg3 can be used for preventing and treating dementia, and can be prepared into medicines or health foods for preventing and treating dementia, thus exploiting a new field for the application of medicinal Radix Ginseng.

2. Series of experimental studies of the present invention demonstrate that 20(R)-ginsenoside Rg3 has outstanding efficacy for preventing and treating dementia. Ginsenoside Rg3 improves the AChE positive nerve fiber density of the cerebral cortex significantly, which shows that ginsenoside Rg3 has a protection effect on the intracerebral cholinergic nerve system with Alzheimer's disease; in experiments of the effect ginsenoside Rg3 on learning and memory of a rat model with Alzheimer's disease, the time of swimming out of rats in the water maze is short and the error time is less, which implies that ginsenoside Rg3 can obviously improve the learning and memory ability of the model rat with Alzheimer's disease; ginsenoside Rg3 can reduce the $\Delta\beta$ content in the cerebrospinal fluid of patients with AD, and ginsenoside Rg3 can effectively improve the patients' intelligence and memory and improve the cognitive function and ability of daily living when used in clinic treatment of AD.

3. 20(R)-ginsenoside Rg3 of the present invention has a strong pharmacological effect, and has significant anti-aging efficacy, quick action, a little toxic or side effect and good safety, and 20(R)-ginsenoside Rg3 can be taken chronically, and has good medicinal prospect.

4. The product material of the present invention is abundant in source, low in cost, safe in clinical use, and simple in preparation process, and can be prepared into various preparations and has small dosing and is easy to use, and thus easily popularizing.

DESCRIPTION OF THE EMBODIMENTS

The advantageous effects of the medicine of the present invention are further illustrated by the following test examples; these examples comprise pharmacodynamic tests of the medicine of the present invention.

Test Example 1 Protection Effect of Ginsenoside Rg3 on Intracerebral Cholinergic Nerve System of Rat Model with Alzheimer's Disease 1. Material:
20(R)-ginsenoside Rg3 (purity>98%), produced by Dalian Fusheng Natural Medicine Development Co., Ltd., with the batch number being: 20120316; by comparison with a standard product provided by National Institute for Food and Drug Control of China and by measured by HPLC, the content accords with the calibration value, and the measured value is 98.2%;

Ginsenoside Rg3 is prepared into a lotion for topical use according to the formula and method of embodiment 7 for standby application; the trial production of the lotion is conducted by Dalian Fusheng Natural Medicine Development Co., Ltd., with the batch number being: 20120425;

Positive medicine: Huperzine A, produced by Shanghai Hongqi Pharmaceutical Factory, with the batch number being: 20111215;

D-galactose: produced by Shanghai Chemical Reagent No. 2 Factory, with the batch number being: 20110607.

Ibotenic acid (IBO), produced by Sigma-Aldrich Co. LLC., with the batch number being: 20101224.

60 preliminary elder female Wistar rats aged 15 months and having body weights of 300-450 g, purchased from the Laboratory animal center of Dalian Medical University, number of certificate of quality: SCXK(13)2012-0003.

2. Method and Result:
2.1 Method
60 Wistar rats each of which having the body weight of 300-500 g are randomly divided into 6 groups, with 10 in each group, and the groups are named a preliminary elder normal control group, a preliminary elder AD model group, a positive medicine Huperzine A group, and high-dose, medium-dose and low-dose of Ginsenoside Rg3 topical preparation groups according to different treatment methods, respectively. The rats are bred in separate cages, each holding 4-5 rats, with natural lighting and random drinking and feeding provided. Physiological saline is injected in the abdominal cavity and grain of each rat in the preliminary elder normal control group; Galactose intraperitoneal injection and IBO intracerebral injection are given to all rats in the preliminary elder AD model group, the positive medicine Huperzine A group, and the high-dose, medium-dose and low-dose Ginsenoside Rg3 topical preparation groups; while the rats in the Huperzine A group and the high-dose, medium-dose and low-dose of Ginsenoside Rg3 topical preparation groups are subjected to D-galactose injection for modeling, rat of each group is given Huperzine A 0.3 mg/kg/d and Ginsenoside Rg3 10, 5, 2.5 mg/kg/d respectively. Ginsenoside Rg3 is applied to both sides of the nose of each rat of Ginsenoside Rg3 topical preparation groups. All the rats are subjected to the medicines continuously for 6 weeks and then intracerebral bilateral Meynert nuclei injection is carried out. Reference is made to a rat cerebral stereotaxic atlas for Meynert nuclei localization, and localization coordinates are AP-0.8 mm, Late 2.6 mm and DV 8.2 mm During intracerebral injection, a rat is anesthetized with 3% pentobarbital sodium (30 mg/kg) and then immobilized to a cerebral stereotaxic apparatus, physiological saline dissolved IBO (injection 1 μl for each side containing 5 μg of IBO) or 1 μl normal saline is injected slowly into a Meynert nucleus, each side takes injection for 5 minutes, and needle retaining for 10 minutes, wherein all the rats are subjected to cerebral perfusion with 4% paraformaldehyde after modeling and are then immobilized for 24 hours, and the brain is put in a sucrose phosphate buffer until brain tissue blocks sink, the blocks are frozen in a incubator and serially sectioned to 40 mm in thickness. The sections are subjected to acetycholinesterase (AChE) histochemical staining by methods recommended by Hedreen, et al. Observation is given to the frontal lobe, the parietal lobe, the occipital lobe and the entorhinal cortex (layer II) as well as parts in a hippocampal CA1 region of the hippocampal formation such as a stratum oriens, a stratum radiatum, a stratum lacunosum-moleculare and a stratum moleculare of dentate gyrus for observing their AChE positive nerve fiber densities, and the AChE positive nerve fiber densities are counted with a number of intersections of positive fibers with a standard grid by using a micrometer used for a microscope.

2.2 Result
Results of acetycholinesterase positive nerve fiber density test for the cortex and hippocampal formation in rats are seen in tables 1 and 2, all results are represented as (X±S), and one-way analysis of variance is carried out using an SAS 6.11 statistical package. A significance level a is equal to 0.05.

TABLE 1

| | | Rat cortical AchE positive nerve fiber density (X ± S) | | | |
|---|---|---|---|---|---|
| Group | Dosage (mg/kg/d) | N Frontal lobe/($10^2 \cdot mm^{-2}$) | Parietal lobe/($10^2 \cdot mm^{-2}$) | N Occipital lobe/($10^2 \cdot mm^{-2}$) | N Entorhinal cortex/($10^2 \cdot mm^{-2}$) |
| Normal group | 10 | 161.1 ± 16.5 | 179.4 ± 25.3 | 156.0 ± 15.7 | 164.4 ± 43.2 |
| Model group | 48 | 122.4 ± 20.9$^{\#\#}$ | 137.9 ± 30.0$^{\#\#}$ | 122.3 ± 6.7$^{\#\#}$ | 111.8 ± 12.9$^{\#\#}$ |
| Huperzine group | 0.3 | 122.1 ± 16.1$^{\#\#}$ | 108.7 ± 15.8$^{\#\#\Delta}$ | 131.6 ± 9.0$^{\Delta}$ | 132.4 ± 19.2$^{\#}$ |
| Ginsenoside Rg3 group | 10 | 143.7 ± 22.1$^{\Delta}$ | 183.9 ± 24.9$^{\#\circ}$ | 167.2 ± 12.9$^{\Delta\Delta\circ}$ | 161.1 ± 18.3$^{\Delta\Delta**\circ}$ |
| | 5 | 130.7 ± 20.8$^{\Delta}$ | 170.9 ± 21.2$^{\#}$ | 160.2 ± 10.2$^{\Delta\Delta}$ | 142.6 ± 11.9 |
| | 2.5 | 122.7 ± 18.6$^{\Delta}$ | 162.9 ± 22.0$^{\#}$ | 145.2 ± 9.2$^{\Delta\Delta}$ | 130.2 ± 15.6 |

Compared with those of the normal group, $^{\circ}P > 0.05$, $^{\#}p < 0.05$ and $^{\#\#}p < 0.01$;
compared with those of the model group, $^{\Delta}p < 0.05$ and $^{\Delta\Delta}p < 0.01$;
compared with those of the huperzine group, *p < 0.05 and **p < 0.01;

From the results in table 1, AChE positive nerve fiber densities for all parts in the high-dose, medium-dose and low-dose of ginsenoside Rg3 groups all gain a significant increase, and the densities for both the frontal lobe and the occipital lobe are significantly different ($P<0.05$ and $P<0.01$) from those in the model group and the Huperzine group and are substantially restored to a normal level ($P>0.05$, in comparison with that of the normal group).

are divided into 6 groups randomly, a normal control group, a sham operated control group, a model control group, and high-dose, medium-dose and low-dose ginsenoside Rg3 groups (10, 5, 2.5 mg/kg/d), wherein each group has 10 animals.

The molding method applying intraperitoneal injection of 0.96% D-galactose prepared by normal saline is applied to rats to make model rat, 5 mL/kg, once daily for 6 continuous

TABLE 2

Rat hippocampal formation AchE positive nerve fiber density ($X \pm S$)

| Group | Dosage (mg/kg/d) | N Stratum oriens/ ($10^2 \cdot mm^{-2}$) | N Stratum radiatum/ ($10^2 \cdot mm^{-2}$) | N Stratum lacunosum-moleculare/ ($10^2 \cdot mm^{-2}$) | N Stratum moleculare of dentate gyrus/ ($10^2 \cdot mm^{-2}$) |
|---|---|---|---|---|---|
| Normal control group | 10 | $152.2 \pm 18.9$ | $134.2 \pm 12.4$ | $91.4 \pm 10.8$ | $141.1 \pm 15.5$ |
| Model control group | 48 | $125.3 \pm 18.5^{\#}$ | $103.4 \pm 19.0^{\#\#}$ | $73.1 \pm 10.8^{\#}$ | $112.4 \pm 16.7^{\#\#}$ |
| Huperzine control group | 0.3 | $138.7 \pm 20.1$ | $121.1 \pm 15.2$ | $83.3 \pm 9.6$ | $120.0 \pm 10.7^{\#}$ |
| Ginsenoside Rg3 group | 10 | $171.1 \pm 16.9^{\Delta}$ | $143.2 \pm 20.5^{\Delta\Delta}$ | $99.2 \pm 17.3^{\Delta}$ | $142.7 \pm 11.9$ |
|  | 5 | $153.0 \pm 22.1^{\Delta}$ | $135.1 \pm 23.9^{\#}$ | $84.2 \pm 10.9^{\Delta\Delta}$ | $131.5 \pm 14.7$ |
|  | 2.5 | $140.1 \pm 20.5^{\Delta}$ | $122.4 \pm 14.4^{\#}$ | $77.2 \pm 9.1^{\Delta\Delta}$ | $119.8 \pm 12.4$ |

Compared with those of the normal group, $^{\circ}P > 0.05$, $^{\#}p < 0.05$ and $^{\#\#}p < 0.01$;
compared with those of the model group, $^{\Delta}p < 0.05$ and $^{\Delta\Delta}p < 0.01$;
compared with those of the huperzine group, $*p < 0.05$ and $**p < 0.01$;

From the results in table 2, AChE positive nerve fiber densities for all parts in the high-dose, medium-dose and low-dose ginsenoside Rg3 groups are higher than those in the model group, and the densities for the stratum oriens, stratum radiatum and stratum moleculare of dentate gyrus in the CA1 region are not significantly different ($P>0.05$ for all) from those in the normal group.

The test results above show that ginsenoside Rg3 can protect the intracerebral cholinergic nervous system of a rat model with Alzheimer's disease.

Test Example 2 Effect of Ginsenoside Rg3 on Learning and Memory of Rat Model with Alzheimer's Disease 1. Material:

20(R)-ginsenoside Rg3 (purity>98%), produced by Dalian Fusheng Natural Medicine Development Co., Ltd., with the batch number being: 20120316; by comparison with a standard product provided by National Institute for the Control of Pharmaceutical and Biological Products of China and measured by PHLC, the content accords with the calibration value, and the measured value is 98.2%.

ginsenoside Rg3 is prepared into an oral emulsion (10 mg/ml) according to the formula and method of embodiment 17 for spare; the trial production of the oral emulsion is conducted by Dalian Fusheng Pharmaceutical Co., Ltd., with the batch number being: 20120320;

Positive medicine. D-galactose (produced by Shanghai Chemical Reagent No. 2 Factory), with the batch number being: 20110607.

Ibotenic acid (IBO), produced by Sigma-Aldrich Co. LLC., with the batch number being: 20101224.

60 preliminary elder female Wistar rats aged 6 months and having body weights of 180-250 g, purchased from the Laboratory animal center of Dalian Medical University, number of certificate of quality: SCXK(13)2012-0003.

2. Method:

Water maze pre-training is performed after feeding for 1 week under the stable condition of laboratory, 60 rats with similar body weights and good flexibility are selected, and weeks. The rat of sham operated control group are injected with equivalent normal saline. The rat groups of the model control group and high-dose, medium-dose and low-dose ginsenoside Rg3 groups are intracranially injected with IBO starting from the $43^{rd}$ day, and each side is slowly injected with 1 μL of IBO, the sham operated group's rats are injected with equivalent normal saline in the same encephalic region (for 4 continuous weeks). The normal control group's rat are without any processing and eat and drink normally. The rats of high-dose, medium-dose and low-dose ginsenoside Rg3 groups are administered intragastrically with ginsenoside Rg3 oral emulsion daily while molding, and are administered for 4 w (weeks) after molding.

The changes of animal behavioristics in each group are tested by channel-type water maze test, and the learning and memory abilities of rats are evaluated by number of entering blind ends and the time needed to reach the terminal. All test results are expressed in mean±standard deviation, and the intergroup difference is subjected to variance analysis by adopting SPSS10.0 statistical package.

3. Result:

The test results are shown in table 3.

TABLE 3

Effect of Rg3 oral emulsion on learning and memory of rat model with Alzheimer's disease ($X \pm S$)

| Group | Dosage (mg/kg/d) | Swimming out time (s) | Error times (time) |
|---|---|---|---|
| Normal control group | 10 | $18.26 \pm 3.41$ | $1.00 \pm 0.75$ |
| Sham operated control group | 10 | $26.42 \pm 5.04$ | $1.65 \pm 0.66$ |
| Model control group | 10 | $59.88 \pm 5.27*$ | $5.44 \pm 0.53*$ |
| Ginsenoside Rg3 group | 10 | $12.26 \pm 3.26^{\#}$ | $1.01 \pm 0.41^{\#}$ |
|  | 5 | $19.26 \pm 3.23^{\#}$ | $1.10 \pm 0.44^{\#}$ |
|  | 2.5 | $32.26 \pm 3.21^{\#}$ | $1.82 \pm 0.43^{\#}$ |

Compared with that of the normal group and the sham operated group, $*p < 0.01$;
compared with that of the model group, $^{\#}p < 0.05$ The shorter the time of animals swimming out of the water maze is and the less the error times are, the greater the learning and memory abilities of animals are. It can be seen from Table 3, the time of swimming out and error times of animals of the model group are obviously more than those of the normal group and sham operated group, and the time of swimming out and error times of animals of the high-dose, medium-dose and low-dose ginsenoside Rg3 groups are obviously less than those of the model group, which indicates that ginsenoside Rg3 can obviously enhance the learning and memory abilities of model rats.

Test Example 3 Effect of Ginsenoside Rg3 on Cerebrospinal Fluid β Amyloid Protein Content of Patients with Alzheimer's Disease 3.1 Test Material:

20(R)-ginsenoside Rg3 (purity>98%), produced by Dalian Fusheng Natural Medicine Development Co., Ltd., with the batch number being: 20120316; by comparison with a standard product provided by National Institute for Food and Drug Control of China and measured by PHLC, the content accords with the calibration value, and the measured value is 98.2%;

ginsenoside Rg3 is prepared into a ginsenoside Rg3 oral solution (10 mg/ml) according to the formula and method of Embodiment 27 for standby application; the trial production of the ginsenoside Rg3 oral solution is conducted by Dalian Fusheng Natural Medicine Development Co., Ltd., with the batch number being: 20120321;

positive control medicine, donepezil (5 mg*7, Eisai (China) Pharmaceutical Co., Ltd.).

3.2 Test Method:

36 patients are all inpatients, and are randomly divided into a ginsenoside Rg3 oral liquid group and a donepezil group, and each group has 18 patients. The ginsenoside Rg3 oral liquid group is orally administered ginsenoside Rg3 oral liquid (10 mg/d) before sleeping; the donepezil group is orally administered 5 mg/d of donepezil prior to sleeping. Both groups take medicine for 12 continuous weeks. 2 ml of cerebrospinal fluid is collected by lumbar puncture, and is stored at −80° C., the β-amyloid protein (Aβ) content is determined by using enzyme-linked immunosorbent assay (ELISA). A revised Hasegawa dementia scale (HDS-R) is used to score, and the scores before and after treatment are compared, increasing in scores means validness, and unchanging or decreasing in scores means invalidness. The enumeration data adopts $\chi^2$ test, the comparison of measurement data adopts t-test, all data is processed by adopting SPSS12.0 statistical software. The test results are shown in table 4.

Analysis on the clinical therapeutic effect of the two groups. The number of patients increased in scores of clinical symptom of the ginsenoside Rg3 oral liquid group is 14, the number of patients constant in scores is 3, and the number of patients decreased in scores is 1, and thus the effective rate is 77.8%. The number of patients increased in scores of clinical symptom of the donepezil group is 13, and the number of patients constant in scores is 3, and the number of patients decreased in scores is 2, the effective rate is 72.2%, and there is no significant difference between the two groups (P>0.05).

TABLE 4

Comparison of scores of before and after treatment and Aβ Content of two groups (n = 18, X ± s)

| Group | Scores of clinical symptom | | Aβ content | |
|---|---|---|---|---|
| | Before treatment | Post treatment | Before treatment | Post treatment |
| Ginsenoside Rg3 group | 12.3 ± 5.2 | 18.7 ± 8.1[#Δ] | 5.9 ± 2.6 | 3.8 ± 1.5[#] |
| Donepezil control group | 13.5 ± 4.2[Δ] | 17.3 ± 9.6[#] | 5.3 ± 1.7 | 4.9 ± 1.2 |

Compared with the situation prior to treatment within the same group: [#]$P < 0.05$ and compared with the donepezil group: [Δ]$P < 0.01$.

It can be known from the results of table 4 that compared with the situations before treatment, the scores of the two groups after treatment are increased obviously (P<0.05), and the scores of the ginsenoside Rg3 group are increased significantly (P<0.05). The Aβ content of the ginsenoside Rg3 group after treatment is decreased obviously (P<0.05), while that of the positive medicine control group after treatment shows no obvious changes (P>0.05). Clinical observation shows that the application of ginsenoside Rg3 in the clinical treatment of AD can effectively enhance intelligence and memory of patents and improve their cognitive functions and activities of daily living. The study indicates that ginsenoside Rg3 can reduce the Aβ content in the cerebrospinal fluid of patents with AD. This may be one of its action mechanisms of treating AD.

Test Example 4 Clinical Research on Effectiveness of Ginsenoside Rg3 on Mild or Moderate Alzheimer's Disease 1. Test Material:

20(R)-ginsenoside Rg3 (purity>98%), produced by Dalian Fusheng Natural Medicine Development Co., Ltd., with the batch number being: 20120316; by comparison with a standard product provided by National Institute for the Control of Pharmaceutical and Biological Products of China and measured by PHLC, the content accords with the calibration value, and the measured value is 98.2%;

ginsenoside Rg3 is prepared into a ginsenoside Rg3 naristillae (10 mg/ml) according to the formula and method of embodiment 29 for standby application; the trial production of the ginsenoside Rg3 naristillae is conducted by Dalian Fusheng Natural Medicine Development Co., Ltd., with the batch number being: 20120324.

2. Test Method:

89 patients with mild or moderate Alzheimer's disease are divided into two groups randomly, one of which take ginsenoside Rg3, and the other placebos. There are 46 patients in the group taking Rg3, with 21 male and 25 female, aged from 58 to 87 (72.6±6.8), scoring from 10 to 24 (17.8±2.3) points in the mini-mental state examination (MMSE); there are 43 patients taking placebos, with 19 male and 24 female aged from 57 to 88 (71.8±8.2), scoring from 10 to 24 (18.2±2.7) points in MMSE. There are no obvious differences between the ginsenoside Rg3 group and the placebo group with respect to gender, age and MMSE scores. The patents in the group taking ginsenoside Rg3 use the ginsenoside Rg3 naristillae once a day for 12 continuous weeks, with 10 mg/ml for each time.

For the patients taking placebos, except that what is used for intranasal administration are placebos, the rest is conducted according to the same administration method as that adopted by those taking ginsenoside Rg3. The placebos are prepared according to the method used to prepare the ginsenoside Rg3 naristillae in embodiment 29. For them, except that ginsenoside Rg3 is not added, the rest is identical to embodiment 29.

The ginsenoside Rg3 naristillae has a concentration of 10 mg/ml, and colors, characters, tastes and dosages of the placebos are the same as those of the ginsenoside Rg3 naristillae. The ginsenoside Rg3 naristillae and the placebos are applied once a day for 12 continuous weeks. Examination is conducted once every four weeks before and after medication, and the examination method is as follows:

(1) MMSE Screening of AD: examining patients' cognitive functions (orientation, memory, computational power, language competence, ability in applying visual-spatial segment etc.; (2) Examining patents' dementia degrees using the clinical dementia rating (CDR); (3) Examining patents' activities of daily living using the activity of daily living scale (ADL).

SPSS statistical software is adopted for examination results. T-test is adopted before and after treatment, and it is also adopted for the ginsenoside Rg3 naristillae group and the placebo control group. For scoring results of MMSE, CDR and ADL of patients with AD before treatment, see table 5

TABLE 5

Scoring results of MMSE, CDR and ADL of patients with AD before treatment (x ± s, points)

| Group | Number | MMSE | CDR | ADL |
|---|---|---|---|---|
| Ginsenoside Rg3 group | 46 | 17.8 ± 2.3 | 1.9 ± 0.3 | 47.2 ± 7.9 |
| Placebo group | 43 | 18.2 ± 2.7 | 2.0 ± 0.2 | 48.3 ± 6.1 |

Notes:
when the group of ginsenoside Rg3 topical preparation is compared with the placebo group, none of the differences among MMSE, CDR and ADL has obvious significance (P > 0.05).

For scoring results of MMSE, CDR and ADL of patients with AD after taking Rg3 and placebos for 12 weeks, see table 6.

TABLE 6

Scoring results of MMSE, CDR and ADL of patients with AD after treatment for 12 weeks (x ± s, points)

| Group | Number | MMSE | CDR | ADL |
|---|---|---|---|---|
| Ginsenoside Rg3 group | 46 | 24.1 ± 2.0** | 1.2 ± 0.2* | 40.5 ± 7.6** |
| Placebo group | 43 | 18.7 ± 2.4 | 2.0 ± 0.2 | 49.5 ± 6.3 |

Notes:
when the ginsenoside Rg3 naristillae group is compared with the placebo group, *P < 0.05, and **P < 0.01.

Cognitive functions (scored by MMSE): the curative effect of the placebo control group indicates that after treatment, the ginsenoside Rg3 group shows an obvious increase in its MMSE score (P<0.01) when compared with the placebo control group; dementia degrees (scored by CDR): after treatment, the ginsenoside Rg3 naristillae group shows a significant decrease in its CDR score (P<0.05) when compared with the placebo control group; activities of daily living (scored by ADL): after treatment, the ginsenoside Rg3 naristillae group shows a very significant decrease in its ADL score (P<0.01) when compared with the placebo control group, and compared with the situation before treatment, the ADL score after treatment is decreased very obviously by 7.1 points (P<0.01).

In sum, the ginsenoside Rg3 is a safe and effective medicine used for treating patients with AD, relieving mild and moderate cognitive impairment, decreased self-care ability of daily living and degree of dementia of patients with AD.

Test Example 5 Clinical Research on Effectiveness of Ginsenoside Rg3 on Mild, Moderate Alzheimer's Disease 1. Test Material:
20(R)-ginsenoside Rg3 (purity>98%), produced by Dalian Fusheng Natural Medicine Development Co., Ltd. with the batch number being: 20120316; by comparison with a standard product provided by National Institute for the Control of Pharmaceutical and Biological Products of China and measured by PHLC, the content accords with the calibration value, and the measured value is 98.2%;

ginsenoside Rg3 is prepared into a ginsenoside Rg3 naristillae (10 mg/ml) according to the formula and method of embodiment 29 for standby application; the trial production of the ginsenoside Rg3 naristillae is conducted by Dalian Fusheng Pharmaceutical Co., Ltd. with the batch number being: 20120324.

2. Test Method:
99 patients with mild or moderate Alzheimer's disease, among which 47 are male, 52 are female, all aged from 55 to 85 (73.5±7.6), MMSE score is 1024 (16.3±2.6) points.

Patients with AD all use the ginsenoside Rg3 naristillae once a day, 10 mg/ml each time, and keep using it for 12 weeks.

Examination is conducted once every four weeks before and after medication, and the medication method is as follows:

(1) MMSE screening of AD: examining patients' cognitive functions (orientation, memory, computational power, language competence, ability in applying visual-spatial etc.; (2) Examining patents' dementia degree using the clinical dementia rating (CDR); (3) examining patents' activities of daily living using the activity of daily living scale (ADL).

SPSS statistical software is adopted for examination results. T-test is adopted before and after treatment, and it is also adopted for the ginsenoside Rg3 naristillae group and the placebo control group.

For scoring results of MMSE, CDR and ADL of patients with AD, see table 7.

TABLE 7

Scoring results of MMSE, CDR, ADL of Patients with AD before and after treatment with Rg3 (x ± s, points)

| Scale name | Before treatment | Treatment for 4 weeks | Treatment for 12 weeks |
|---|---|---|---|
| MMSE | 16.3 ± 2.6 | 17.1 ± 1.9* | 19.8 ± 1.7** |
| CDR | 2.1 ± 0.3 | 1.9 ± 0.2 | 1.5 ± 0.2* |
| ADL | 49.6 ± 8.2 | 48.2 ± 7.9 | 42.5 ± 7.3** |

Notes:
comparison is carried out on the self-control group before and after treatment, *P < 0.05, and **P < 0.01.

Cognitive functions (scored by MMSE): the effectiveness after treatment for 12 weeks is significantly increased, the MMSE score is increased by 3.5 points (P<0.01), and the MMSE score has been increased obviously after the treatment for 4 weeks (P<0.05). The degree of dementia (scored by CDR): the effectiveness after treatment for 12 weeks is significantly decreased compared with that of before the treatment, the CDR score is decreased by 0.6 points (P<0.05). The ability of daily living (scored by ADL): the curative effect after treatment is obviously decreased compared with that before the treatment, the ADL score is decreased by 7.1 points (P<0.01).

In sum, the ginsenoside Rg3 is a safe and effective medicine used for treating patients with AD, relieving mild and moderate cognitive impairment, decreased self-care ability of daily living and degree of dementia of patients with AD.

The present invention will be described in further details with the following embodiments.

Embodiment 1

1. Preparing raw materials according to the following formula
20(R)-ginsenoside Rg3 (98%) 2 g; azone 2 g; propylene glycol 10 ml, and an appropriate amount of ethanol (65%);
2. Adding ginsenoside Rg3, azone, propylene glycol into ethanol (65%), wherein the total volume after mixing is 85 ml;
3. Adding the mixture with a total volume of 85 ml into a 500 ml flask, heating to 50-55° C., stirring while maintaining the temperature at 50-55° C. until the 20(R)-ginsenoside Rg3 is completely dissolved, stopping heating after stirring for 30 minutes, cooling to room temperature (15-25° C.), and supplementing ethanol (65%) to 100 ml to obtain a ginsenoside Rg3 liniment.

Embodiment 2

1. Preparing raw materials according to the following formula
20(R)-ginsenoside Rg3 (98%) 2 g; azone 2 g; polyethylene glycol 400 10 ml; and an appropriate amount of ethanol (70%);
2. Adding ginsenoside Rg3, azone, polyethylene glycol 400 into ethanol (70%), wherein the total volume after mixing is 85 ml;
3. Adding the mixture (85 ml) into a 500 ml flask, heating to 50-55° C., stirring while maintaining the temperature at 50-55° C. until 20(R)-ginsenoside Rg3 is completely dissolved, stopping heating after stirring for 30 minutes, cooling to room temperature (15-25° C.), and supplementing ethanol (70%) to 100 ml to obtain a ginsenoside Rg3 lotion.

Embodiment 3

1. Preparing raw materials according to the following formula
20(R)-ginsenoside Rg3 (98%) 2 g; azone 2 g; polyethylene glycol 600 10 ml; and an appropriate amount of ethanol (70%);
2. Adding ginsenoside Rg3, azone, polyethylene glycol 600 into ethanol (70%), wherein the total volume after mixing is 85 ml;
3. Adding the mixture (85 ml) into a 500 ml flask, heating to 50-55° C., stirring while maintaining the temperature at 50-55° C. until 20(R)-ginsenoside Rg3 is completely dissolved, stopping heating after stirring for 30 minutes, cooling to room temperature (15-25° C.), and supplementing ethanol (70%) to 100 ml to obtain a ginsenoside Rg3 lotion.

Embodiment 4

1. Preparing raw materials according to the following formula
20(R)-ginsenoside Rg3 (63%) 2 g; azone 2 g; polyethylene glycol 200 10 ml; and an appropriate amount of ethanol (65%);
2. Adding ginsenoside Rg3, azone, polyethylene glycol 200 into ethanol (60%), wherein the total volume after mixing is 85 ml;
3. Adding the mixture with a total volume of 85 ml into a 500 ml flask, heating to 50-55° C., stirring while maintaining the temperature at 50-55° C. until 20(R)-ginsenoside Rg3 is completely dissolved, stopping heating after stirring for 30 minutes, cooling to room temperature (15-25° C.), and supplementing ethanol (65%) to 100 ml to obtain a ginsenoside Rg3 lotion.

Embodiment 5

1. Preparing raw materials according to the following ratio
20(R)-ginsenoside Rg3 (30%) 1 g, glycerol 2 g, polyethylene glycol 200 10 ml, and an appropriate amount of ethanol (70%);
2. Adding ginsenoside Rg3, azone, and polyethylene glycol 200 into ethanol (70%), wherein the total volume after mixing is 85 ml;
3. Adding the mixture with a total volume of 85 ml into a 500 ml flask, heating to 50-55° C., stirring while maintaining the temperature at 50-55° C. until 20(R)-ginsenoside Rg3 is completely dissolved, stopping heating after stirring for 30 minutes, cooling to room temperature (15-25° C.), and supplementing ethanol (70%) to 100 ml to obtain a ginsenoside Rg3 lotion.

Embodiment 6

1. Preparing raw materials according to the following formula
20(R)-ginsenoside Rg3 (98%) 1 g; Medium-Chain Triglyceride 20 g; propylene glycol 10 ml; phosphatide 20 g; and an appropriate amount of water for injection;
2. Adding ginsenoside Rg3, Medium-Chain Triglyceride, propylene glycol, and phosphatide into a small amount of water for injection, heating to 65-70° C., stirring to dissolve ginsenoside Rg3, adding the evenly stirred mixture into a homogenizer to be homogenized, cooling to room temperature (15-25° C.), and supplementing water for injection to 100 ml to obtain a ginsenoside Rg3 emulsion for injection.

The medium-chain triglyceride used in the embodiments of the invention, i.e. decanoyl/octanoyl-glycerides, is a semisynthetic natural functional lipid, which is safe and reliable according to years of application at home and abroad and has broad application field and use value, being abbreviated to MCT in Europe and America. The product can be widely applied to medicine, food, health care products, cosmetics and the like.

Embodiment 7

1. Preparing raw materials according to the following formula
20(R)-ginsenoside Rg3 (98%) 2 g; azone 2 g; Radix Ginseng oil 0.5 g; propylene glycol 10 ml; and an appropriate amount of ethanol (65%);
2. Adding ginsenoside Rg3, azone, Radix Ginseng oil, and propylene glycol into ethanol (65%), wherein the total volume after mixing is 85 ml;
3. Adding the mixture with a total volume of 85 ml into a 500 ml flask, heating to 50-55° C., stirring while maintaining the temperature at 50-55° C. until 20(R)-ginsenoside Rg3 is completely dissolved, stopping heating after stirring for 30 minutes, cooling to room temperature (15-25° C.), and supplementing ethanol (65%) to 100 ml to obtain a ginsenoside Rg3 lotion.

Embodiment 8

1. Preparing raw materials according to the following ratio
20(R)-ginsenoside Rg3 (98%) 2 g; azone 2 g; Radix Curcumae oil 1 g; polyethylene glycol 400 10 ml; and an appropriate amount of ethanol (70%).
2. Adding ginsenoside Rg3, azone, Radix Curcumae oil, and polyethylene glycol 400 into ethanol (70%), wherein the total volume after mixing is 85 ml;
3. Adding the mixture with a total volume of 85 ml into a 500 ml flask, heating to 50-55° C., stirring while maintaining the temperature at 50-55° C. until 20(R)-ginsenoside Rg3 is completely dissolved, stopping heating after stirring for 30 minutes, cooling to room temperature (15-25° C.), and supplementing ethanol (70%) to 100 ml to obtain a ginsenoside Rg3 lotion.

Embodiment 9

1. Preparing raw materials according to the following ratio
20(R)-ginsenoside Rg3 (98%) 2 g, azone 2 g, Moschus oil 0.05 g, polyethylene glycol 600 10 ml, and an appropriate amount of ethanol (70%);
2. Adding ginsenoside Rg3, azone, Moschus oil, and polyethylene glycol 600 into ethanol (70%), wherein the total volume after mixing is 85 ml;
3. Adding the mixture with a total volume of 85 ml into a 500 ml flask, heating to 50-55° C., stirring while maintaining the temperature at 50-55° C. until 20(R)-ginsenoside Rg3 is completely dissolved, stopping heating after stirring for 30 minutes, cooling to room temperature (15-25° C.), and supplementing ethanol (70%) to 100 ml to obtain a ginsenoside Rg3 lotion.

Embodiment 10

1. Preparing raw materials according to the following ratio
20(R)-ginsenoside Rg3 (63%) 2 g, azone 2 g, Rhizoma Chuanxiong oil 0.2 g, polyethylene glycol 200 10 ml, and an appropriate amount of ethanol (65%);
2. Adding ginsenoside Rg3, azone, Rhizoma Chuanxiong oil, and polyethylene glycol 200 into ethanol (65%), wherein the total volume after mixing is 85 ml;
3. Adding the mixture with a total volume of 85 ml into a 500 ml flask, heating to 50-55° C., stirring while maintaining the temperature at 50-55° C. until 20(R)-ginsenoside Rg3 is completely dissolved, stopping heating after stirring for 30 minutes, cooling to room temperature (15-25° C.), and supplementing ethanol (65%) to 100 ml to obtain a ginsenoside Rg3 lotion.

Embodiment 11

1. Preparing raw materials according to the following ratio
20(R)-ginsenoside Rg3 (30%) 2 g, glycerol 2 g, Rhizoma Acori Tatarinowii oil 0.2 g, polyethylene glycol 200 10 ml, and an appropriate amount of ethanol (70%).
2. Adding ginsenoside Rg3, azone, Rhizoma Acori Tatarinowii oil, and polyethylene glycol 200 into ethanol (70%), wherein the total volume after mixing is 85 ml;
3. Adding the mixture with a total volume of 85 ml into a 500 ml flask, heating to 50-55° C., stirring while maintaining the temperature at 50-55° C. until 20(R)-ginsenoside Rg3 is completely dissolved, stopping heating after stirring for 30 minutes, cooling to room temperature (15-25° C.), and supplementing ethanol (70%) to 100 ml to obtain a ginsenoside Rg3 lotion.

Embodiment 12

1. Preparing raw materials according to the following ratio
20(R)-ginsenoside Rg3 (98%) 1 g, medium-chain triglyceride 20 g, borneolum syntheticum 0.5 g, propylene glycol 10 ml, phosphatide 20 g, and an appropriate amount of water for injection; 2. Adding ginsenoside Rg3, medium-chain triglyceride, borneol, propylene glycol, and phosphatide to a small amount of water for injection, heating to 65-70° C., and stirring to dissolve the ginsenoside Rg3, adding the evenly stirred mixture to a homogenizer to be homogenized, cooling to room temperature (15-25° C.), and supplementing the water for injection to 100 ml to obtain a ginsenoside Rg3 emulsion for injection.

Embodiment 13

1. Preparing raw materials according to the following ratio
20(R)-ginsenoside Rg3 (98%) 2 g, azone 2 g, calculus bovis artifactus 0.5 g, propylene glycol 10 ml, and an appropriate amount of ethanol (65%);
2. Adding ginsenoside Rg3, azone, calculus bovis artifactitus, and propylene glycol into ethanol (65%), wherein the total volume after mixing is 85 ml;
3. Adding the mixture with a total volume of 85 ml into a 500 ml flask, heating to 50-55° C., stirring while maintaining the temperature at 50-55° C. until 20(R)-ginsenoside Rg3 is completely dissolved, stopping heating after stirring for 30 minutes, cooling to room temperature (15-25° C.), and supplementing ethanol (65%) to 100 ml to obtain a ginsenoside Rg3 lotion.

Embodiment 14

1. Preparing raw materials according to the following ratio
20(R)-Ginsenoside Rg3 (98%) 2 g, azone 2 g, *styrax* 0.5 g, polyethylene glycol 400 10 ml, and n appropriate amount of ethanol (70%);
2. Adding ginsenoside Rg3, azone, *styrax*, polyethylene glycol into ethanol (70%), wherein the total volume after mixing is 85 ml;
3. Adding the mixture with a total volume of 85 ml into a 500 ml flask, heating, stirring for 30 minutes to dissolve the mixture, cooling naturally, and supplementing 70% ethanol to 100 ml to obtain the a ginsenoside Rg3 topical preparation.

Embodiment 15

1. Preparing raw materials according to the following ratio
20(R)-ginsenoside Rg3 (98%) 1 g, soybean oil 20 g, propylene glycol 10 ml, phosphatide powder 20 g, and an appropriate amount of distilled water;
2. Adding ginsenoside Rg3, soybean oil, propylene glycol, and phosphatide powder to a small amount of distilled water, heating to 65-70° C., and stirring to dissolve the ginsenoside Rg3, adding the evenly stirred mixture to a homogenizer to be homogenized, cooling to room temperature (15-25° C.), and supplementing the distilled water to 100 ml to obtain a ginsenoside Rg3 oral emulsion.

Embodiment 16

1. Preparing raw materials according to the following ratio
20(R)-ginsenoside Rg3 (98%) 1 g, soybean oil (for injection) 50 g, medium-chain triglyceride 100 g;

2. Heating ginsenoside Rg3 (98%), soybean oil, medium-chain triglyceride to 80-85° C., and stirring to dissolve ginsenoside Rg3 to obtain a ginsenoside Rg3 injection.

Embodiment 17

1. Preparing raw materials according to the following ratio
    20(R)-ginsenoside Rg3 (98%) 1 g, Radix Ginseng volatile oil 2 g, propylene glycol 10 ml, Rhizoma Chuanxiong oil 0.5 g, phosphatide 20 g, and an appropriate amount of distilled water;
2. Adding ginsenoside Rg3, Radix Ginseng volatile oil, propylene glycol, Rhizoma Chuanxiong oil and phosphatide to a small amount of distilled water, heating to 65-70° C., and stirring to dissolve the ginsenoside Rg3, adding the evenly stirred mixture to the homogenizer to be homogenized, cooling to room temperature (15-25° C.), and supplementing the distilled water to 100 ml to obtain a ginsenoside Rg3 oral emulsion.

Embodiment 18

1. Preparing raw materials according to the following ratio
    20(R)-ginsenoside Rg3 (purity 85%) 1 g, Rhizoma Acori Tatarinowii oil 20 g, propylene glycol 10 ml, phosphatide powder 20 g, and an appropriate amount of distilled water;
2. Adding ginsenoside Rg3, Rhizoma Acori Tatarinowii oil, propylene glycol, and phosphatide powder to a small amount of distilled water, heating to 65-70° C., and stirring to dissolve the ginsenoside Rg3, adding the evenly stirred mixture to a colloid mill to be treated, cooling to room temperature (15-25° C.), and supplementing the distilled water to 100 ml to obtain a ginsenoside Rg3 oral emulsion.

Embodiment 19

1. Preparing raw materials according to the following ratio
    20(R)-ginsenoside Rg3 (purity 63%) 1 g, tulip oil 10 g, and medium-chain triglyceride 100 g;
2. Heating ginsenoside Rg3, tulip oil, and medium-chain triglyceride to 50-55° C., and stirring to dissolve ginsenoside Rg3 to obtain a ginsenoside Rg3 oral liquid.

Embodiment 20

1. Preparing raw materials according to the following ratio
    20(R)-ginsenoside Rg3 (purity 30%) 1 g, Rhizoma Chuanxiong oil 10 g, medium-chain triglyceride 100 g;
2. Heating ginsenoside Rg3, Rhizoma Chuanxiong oil, medium-chain triglyceride to 50-55° C., and stirring to dissolve ginsenoside Rg3 to obtain a ginsenoside Rg3 oral liquid.

Embodiment 21

1. Preparing raw materials according to the following ratio
    20(R)-ginsenoside Rg3 (purity 98%) 1 g, Moschus oil 2 g, propylene glycol 10 ml, phosphatide 20 g, and an appropriate amount of distilled water.
2. Adding ginsenoside Rg3, Moschus oil, propylene glycol, and phosphatide to a small amount of distilled water, heating to 65-70° C., stirring to dissolve the ginsenoside Rg3, adding the evenly stirred mixture to a homogenizer to be homogenized, cooling to room temperature (15-25° C.), and supplementing the distilled water to 100 ml to obtain a ginsenoside Rg3 oral emulsion.

Embodiment 22

1. Preparing raw materials according to the following ratio
    20(R)-ginsenoside Rg3 (purity 98%) 1 g, medium-chain triglyceride 20 g, Moschus oil 3 g, propylene glycol 10 ml, phosphatide 20 g, an appropriate amount of water for injection.
2. Adding ginsenoside Rg3, medium-chain triglyceride, Moschus oil, propylene glycol, and phosphatide to a small amount of water for injection, heating to 65-70° C., stirring to dissolve the ginsenoside Rg3, adding the evenly stirred mixture to a homogenizer to be homogenized, cooling to room temperature (15-25° C.), and supplementing the water for injection to 100 ml to obtain a ginsenoside Rg3 emulsion for injection.

Embodiment 23

1. Preparing raw materials according to the following ratio
    20(R)-ginsenoside Rg3 (purity 98%) 1 g, medium-chain triglyceride 20 g, Rhizoma Acori Tatarinowii oil 2 g, polyethylene glycol 100 10 ml, phosphatide 20 g, and an appropriate amount of water for injection.
2. Adding ginsenoside Rg3, medium-chain triglyceride, Rhizoma Acori Tatarinowii oil, propylene glycol, and phosphatide to a small amount of water for injection, heating to 65-70° C., stirring to dissolve the ginsenoside Rg3, adding the evenly stirred mixture to a homogenizer to be homogenized, cooling to room temperature (15-25° C.), and supplementing the water for injection to 100 ml to obtain a ginsenoside Rg3 emulsion for injection.

Embodiment 24

1. Preparing raw materials according to the following ratio
    20(R)-ginsenoside Rg3 (purity 98%) 1 g, sucrose 50 g, Rhizoma Acori Tatarinowii oil 2 g, dextrin 100 g, and silicon dioxide 5 g;
2. Taking the formulated amount of Rhizoma Acori Tatarinowii oil, and silicon dioxide, and evenly mixing; making silicon dioxide fully adsorb Rhizoma Acori Tatarinowii oil; adding ginsenoside Rg3, sucrose, and dextrin; granulating with 70% ethanol, sieving, and drying at 65-70° C. to obtain ginsenoside Rg3 granules.

Embodiment 25

1. Preparing raw materials according to the following ratio
    20(R)-ginsenoside Rg3 (purity 98%) 1 g, sucrose 50 g, Rhizoma Chuanxiong oil 2 g, dextrin 100 g, and silicon dioxide 3 g;
2. Taking the formulated amount of Rhizoma Chuanxiong oil, and silicon dioxide, and mixing evenly, making silicon dioxide fully adsorb Rhizoma Chuanxiong oil; adding ginsenoside Rg3, sucrose, and dextrin; granulating with 70% ethanol, sieving, and drying at 65-70° C. to obtain ginsenoside Rg3 granules

Embodiment 26

1. Preparing raw materials according to the following ratio
   20(R)-ginsenoside Rg3 (purity 98%) 1 g, starch 100 g, Radix Ginseng oil 3 g, microcrystalline cellulose 100 g, β-cyclodextrin 10 g, and talcum powder 1 g;
2. Taking the formulated amount of β-cyclodextrin, adding 100 ml of water to dissolve the β-cyclodextrin, maintaining the temperature at 70° C. with a water bath, adding Radix Ginseng oil, stirring the mixture for 30 minutes; taking out the solution, cooling, and filtering the precipitate to obtain an inclusion compound of Radix Ginseng oil. adding ginsenoside Rg3, starch, and microcrystalline cellulose, granulating with an appropriate amount of ethanol; sieving, milling, adding talcum powder, and performing the mixture to obtain ginsenoside Rg3 tablets

Embodiment 27

1. Preparing raw materials according to the following ratio
   20(R)-ginsenoside Rg3 (purity 98%) 1 g, sucrose 50 g, Rhizoma Chuanxiong oil 3 g, β-cyclodextrin 10 g, sodium benzoate 2 g, and an appropriate amount of distilled water;
2. Taking the formulated amount of β-cyclodextrin, adding water to dissolve β-cyclodextrin, maintaining the temperature at 70° C. with a water bath, adding Rhizoma Chuanxiong oil, stirring the mixture for 30 minutes; taking out the solution, cooling, and filtering the precipitate to obtain an inclusion compound of Rhizoma Chuanxiong oil. Adding ginsenoside Rg3, sucrose, and sodium benzoate, and adding the distilled water to 500 ml to obtain ginsenoside Rg3 oral liquid.

Embodiment 28

1. Preparing raw materials according to the following ratio
   20(R)-ginsenoside Rg3 (purity 98%) 1 g, Moschus oil 1 g, 90% ethanol 10 ml, glycerol 5 g, an appropriate amount of F12/F114 (propellant of (Freon) compound). The total amount of all raw materials is 100 g;
2. Weighing accurately the formulated amount of ginsenoside Rg3, and Moschus oil, adding into ethanol to dissolve ginsenoside Rg3 and Moschus oil, then adding glycerol, mixing evenly to prepare a solution, subpackaging the solution with aerosol containers, mounting valves, rolling tight sealing caps, and then filing mixed propellant F12/F114.

Embodiment 29

1. Preparing raw materials according to the following ratio
   20(R)-ginsenoside Rg3 (purity 98%) 1 g, Rhizoma Chuanxiong oil 1 g, ethanol (60%) 10 ml, polyethylene glycol 200 5 ml, glycerol 20 g, and an appropriate amount of water for injection;
2. Weighing accurately ginsenoside Rg3 (1 g), and Rhizoma Chuanxiong oil (1 g), adding 10 ml of 60% ethanol, 5 ml of polyethylene glycol 200, and 20 g of glycerol, heating the mixture at a low temperature, stirring to dissolve the mixture, and adding the water for injection to obtain a ginsenoside Rg3 naristillae.

Orifice-opening medicinal used in the embodiments of the invention, such as Radix Ginseng (volatile) oil, Rhizoma Chuanxiong (volatile) oil, Moschus (volatile) oil, Radix Curcumae (volatile) oil, Rhizoma Acori Tatarinowii (volatile) oil, borneolum syntheticum, calculus bovis artifactus, tulip oil and *styrax*, are mainly effective in opening the orifices with herbal aromatics and inducing resuscitation and are clinically used to treat diseases such as stroke and delirium. Studies of recent years discover that inducing resuscitation drugs used to treat brain diseases by affecting the blood-brain barrier (BBB), some of the resuscitation-inducing drugs can promote permeability of other medicines so that these drugs exert their main acting mechanism of inducing resuscitation to restore consciousness, and it is speculated that the mechanism may be the theoretical basis of heart meridian distribution of these medicines. For example, borneolum syntheticum can improve blood-brain barrier permeability and promote medicines to enter brain tissues, and the resuscitation-inducing drugs such as Moschus, benzoin and *styrax* have some opening action on the blood-brain barrier for rats under physiological conditions and can promote medicines to enter brain tissues.

During preparation of Rg3 preparations, components such as azone, polyethylene glycol, ethanol and traditional Chinese medicine volatile oils are added into each prescription, the addition of these components enables the blood-brain barrier to open so that Rg3 can enter brain tissues and exert anti-dementia action, and the present invention also uses "Detection test for ginsenoside Rg3 medicines of different dosage forms absorbed through blood-brain barrier upon administration in embodiment 30" to verify again that Rg3 has entered the brains of the rats under physiological conditions. Therefore, all of the prescriptions and processes designed in the invention and prepared samples have an anti-dementia action.

The Radix Ginseng oil used in the embodiments of the invention is purchased from Jiangxi Ji'an City Qingyuan District Hualong Spice Oil Co., Ltd.; the Rhizoma Chuanxiong oil is purchased from Jiangxi Ji'an City Senhai Spice Co., Ltd.; the Moschus oil is purchased from Jiangxi Baicao Pharmaceutical Co., Ltd.; the Rhizoma Acori Tatarinowii is purchased from Xi'an Ruiying Biotechnology Co., Ltd.; the tulipa oil is purchased from Jiangxi Bencao Natural Spice Oil Co., Ltd.; the Radix Curcumae oil is purchased from Jiangxi Hengcheng Natural Spice Oil Co., Ltd.; the Radix Ginseng volatile oil is purchased from Jiangxi Huanqiu Natural Spice Co., Ltd.

The Radix Ginseng oil comprises main components: an essential oil ≥11% in content and <30 KOHmg/g in acid value, a ginsenoside, ginseng polysaccharides, a volatile oil, amino acids and polypeptides, as well as β-elemene, β-gurjunene, β-panacene, α-panacene, caryophyllene, β-farnesene and palmitic acid; the Radix Ginseng volatile oil comprises main components: sesquiterpenes about 40%, and oxygen compounds and long-chain alkanes.

Embodiment 30 Detection Test for Ginsenoside Rg3 Medicines of Different Dosage Forms Absorbed Through Blood-Brain Barrier Upon Administration 1. Test Material
1.1 Animal SD rats, 50 days old, male, about 260 g in body weight, clean animal, purchased from the Laboratory animal center of Dalian Medical University, laboratory animal license NO: SCXK (Liao) 2004-0017.

1.2 Instrument and Reagent

Rat cerebrospinal fluid suction apparatus: large and small surgical scissors, tweezers, hemostats, and syringes (1 mL); a graduated scale, trays, aseptic cotton balls, iodophor, Angle Two brain stereotaxic apparatus (by Paxinos Atlas USA Myneurolab company), a low speed dental drill (by Grobet File Co. Of America Inc), a micro-injection pump (by American company of KD Scientific Inc), and 10 μL, and 100 μL, microsyringes (by American company of Hamilton Inc).

Instrument for measuring Rg3 medicine content in rat cerebrospinal fluid: API type-4000 triple quadrupole tandem mass spectrometer, fitted with an ion-spray ion source and an Analysis 1.3 data processing system, by American company of Applied Biosystems Inc; Agilent 1100 high-performance liquid chromatography infusion pump, an autosampler, by Agilent Technologies Co. Ltd. Chromatographic columns Nucleosil C18 columns (50*4.6 mm I.D., 5 μm in particle size), by Dalian Elite Analytical Instruments Co., Ltd.

1.3 Instrument and Medicine

Ginsenoside Rg3 preparations prepared in embodiments 1-2, embodiments 6-14, embodiments 16-21 and embodiments 25-29.

2. Test Method (1) Administration of Different Dosage Forms of Ginsenoside Rg3

1) Oral administration: an oral preparation of ginsenoside Rg3 is given to SD rats by lavage, the medicines of all high-dosage, medium-dosage and low-dosage groups are: 20, 10 and 5 mg/kg (the dosage above is pure dosage of Rg3)/bid, respectively, and each dosage group has 18 rats;

2) External administration: ginsenoside Rg3 is given to SD rats, an external medicine is applied to dampness-eliminating Touqiao acupoint or the both sides of nose, neck and back of ear, the medicines of all high-dosage, medium-dosage and low-dosage groups are: 10, 5, and 2.5 mg/kg (namely amounts of Rg3 are respectively 10, 5 and 2.5 mg/kg)/bid, respectively, and each dosage group has 18 rats;

3) Administration by injection: an intravenous injection of ginsenoside Rg3 at the tail of rat is given to SD rat, wherein the high-dosage, medium-dosage and low-dosage groups respectively are: 6, 3, 1.5 mg/kg/bid, and each dosage group has 18 rats.

(2) Rat Cerebrospinal Fluid Suction

Rat cerebrospinal fluid is sucked after orally, topically and injection administering different preparations of ginsenoside Rg3 for 4 hours. The rat cerebrospinal fluid is sucked by using a method of scarifying endorhachis under direct vision, referring to a method of a document (Improvement on a suction method of the rat cerebrospinal fluid. Journal of Hebei Medical University, 2010 (31)2: 125-127). Each rat is anesthetized with 10% chloral hydrate by intraperitoneal injection, the head of the rat is fixed by brain straight body positioning ear rods and front tooth rods, the occipital region is sheared and sterilized, and a longitudinal incision (about 2 cm) is cut along the posterior midline, and the muscles at the dorsal part of napex are bluntly separated with a pair of scissors. The bottommost layer muscles attached to the occipital bone L are scraped away by the back of a scalpel to avoid bleeding, the wound is washed with distilled water after exposing atlanto-occipital fascia, after cleaning is carried out with a sterile cotton ball, the endorhachis is longitudinally scarified with a scalpel by 0.3 cm, and the flow of the clear cerebrospinal fluid can be seen, a 100 μl microsyringe (round head) prepared in advance is placed at the crevasse to suck the cerebrospinal fluid, each rat is sucked for 2 times, and 100 μl for each suction; the cerebrospinal fluids of 3 rats in each dosage group are mixed evenly to be prepared into one sample, and 6 biological samples are prepared in each dosage group.

The rats without being administered with ginsenoside Rg3 are blank control.

(3) Determination of Ginsenoside Rg3 Content in Cerebrospinal Fluid of Rats Administered with Different Dosage Forms The medicine concentrations in the rat cerebrospinal fluid are determined by LC/MS/MS methods.

Medicine:

ginsenoside Rg3 standard reference substance, purchased from National Institute for the Control of Pharmaceutical and Biological Products of China, with the batch number being: 110804-200603.

ginsenoside Rg3 raw material, produced by Dalian Fusheng Natural Medicine Development Co., Ltd., with the batch number being: 2012303, and the content is 98.2% after HPLC calibration of ginsenoside Rg3 standard reference substance;

the content determination method of the high-dosage, medium-dosage and low-dosage ginsenoside Rg3 groups in different preparations of other ginsenoside Rg3 is the same as the calibration method of ginsenoside Rg3 raw material, and the test results of the content of ginsenoside Rg3 of different preparations are shown in the test results in detail.

Reagent:

acetonitrile, methanol, ethyl acetate are all chromatographic pure reagents, and are purchased from Thermo Fisher Scientific Inc. and Tianjin Kangke Deke Science and Technology Ltd. respectively; the saline solution is purchased from Shenyang Zhiying pharmaceutical plant.

Tissue Sample Processing

Taking 200 μl of cerebrospinal fluid after sucking, adding 100 μl of methanol solution, 100 μl of internal standard solution (100 ng/ml dioscin and methanol solution) and 0.5 ml of water respectively and mixing uniformly, adding 3 ml of ethyl acetate, eddying for 1 minute, oscillating for 10 minutes, and centrifuging (4000 rpm) for 8 minutes, separating the supernatant and blow-drying under air flow of 40° C., dissolving the residue in 200 μl moving phase and taking 20 μl for analysis.

Chromatographic condition: the moving phase is methanol-acetonitrile-10 mmol/l ammonium acetate solution (47.5:47.5:5, v/v), the flow rate is 0.7 ml/min, and the column temperature is room temperature.

Figure 1:
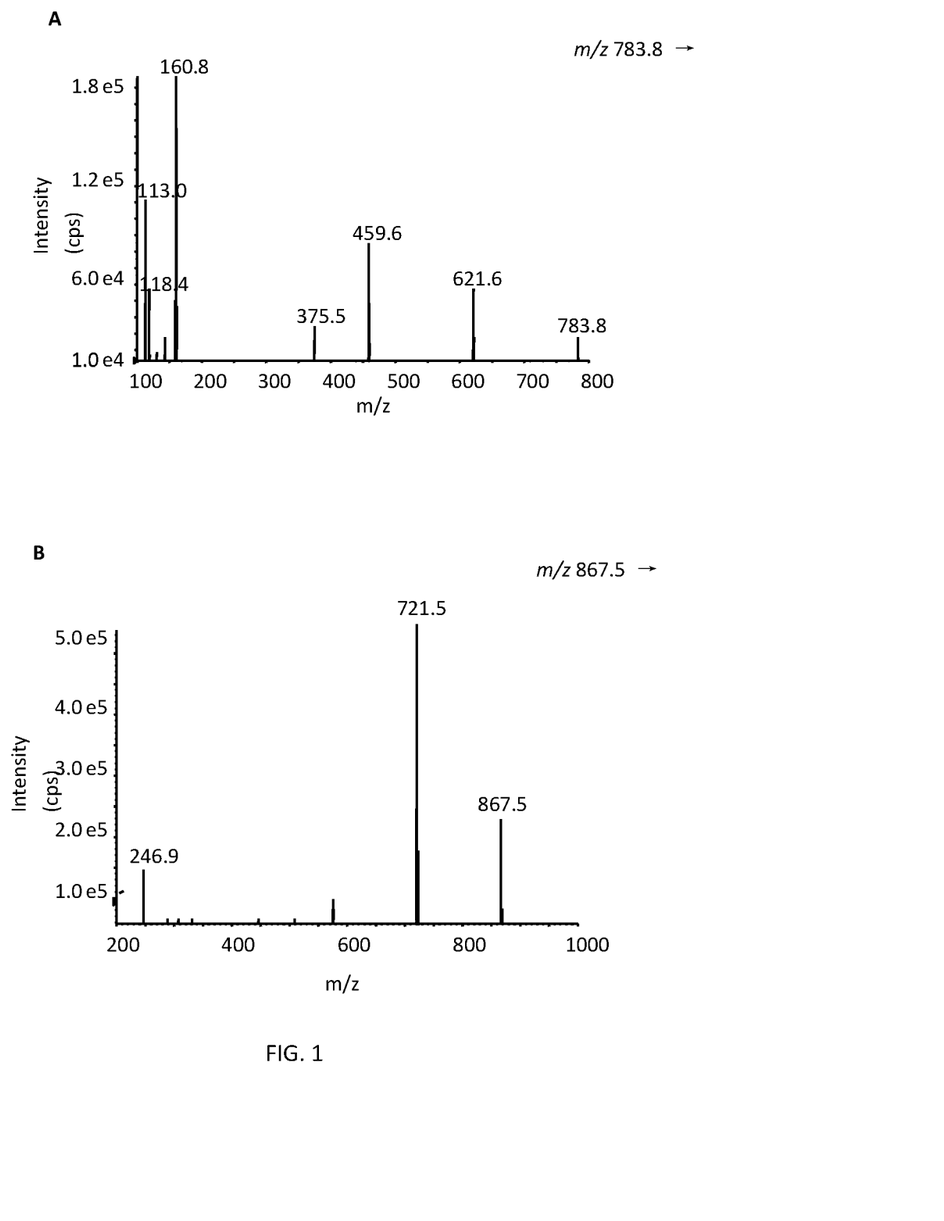
FIG. 1 shows secondary full-scan mass spectrums of quasi-molecular ion [M-H]− of Ginsenoside Rg3 (A) and Dioscin (B)

Mass spectrum condition: ionic propulsion voltage: −3500 V; pressure of gas 1 within the source (GS1, N2): 30 p.s.i.; pressure of gas 2 (GS2, N2): 30 p.s.i.; pressure of curtain gas (N2): 15 p.s.i.; pressure of collision gas (N2): 3 p.s.i.; temperature within the source: 500° C. Detection mode: negative ion detection; Scanning manner: the reaction monitoring (MRM) manner is selected, and the ionic reactions for qualitative analysis are m/z 783.8→m/z 160.8 (ginsenoside Rg3), m/z 867.5→m/z 721.5 (internal standard, dioscin) respectively. The corresponding secondary full-scan mass spectrum is shown in FIG. 1.

Specificity of the Method

The cerebrospinal fluid of blank rat without being administrated with medicine is taken, besides no internal standard solution addition and then additional addition of 100 μl methanol, the balance is operated under "tissue sample treatment" item to obtain the chromatogram of the blank sample; the ginsenoside Rg3 standard reference substance solution (2 ng/ml) and internal standard solution (100 ng/ml) are added to the blank rat cerebrospinal fluid to obtain corresponding chromatogram according to the same operation; the chromatogram of the cerebrospinal fluid sample of rat after administrating is obtained according to the same treatment.

Figure 2:
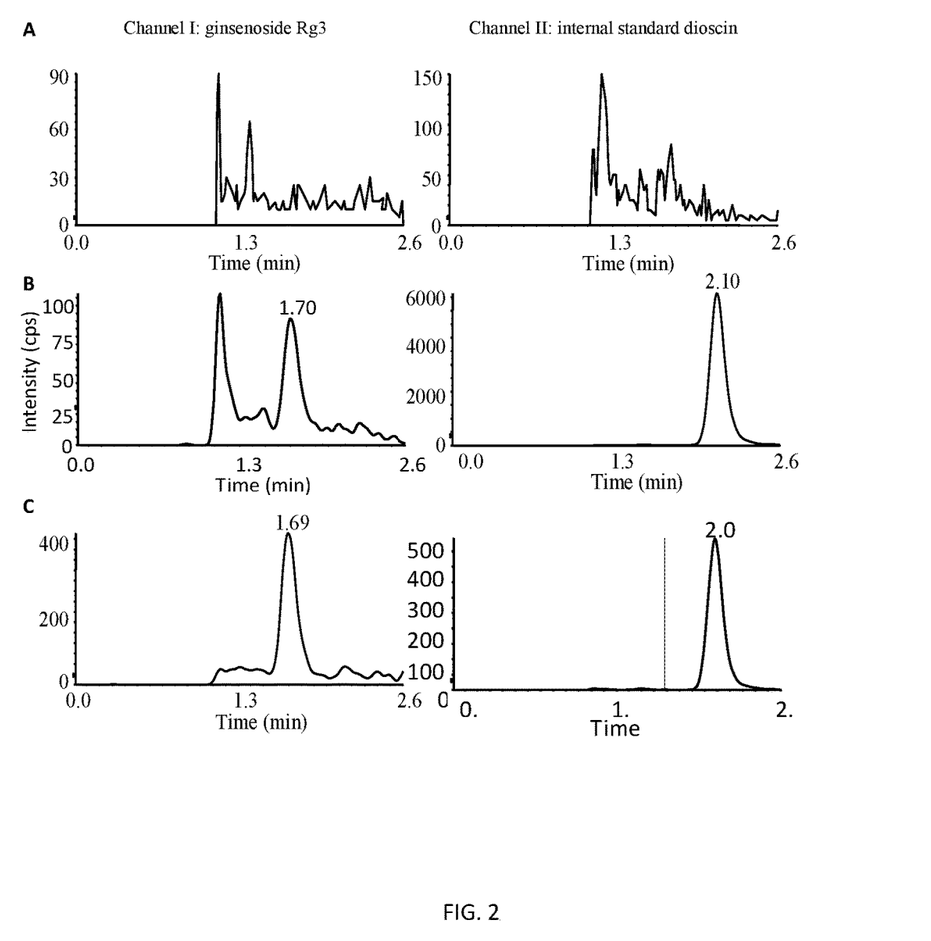
FIG. 2 shows typical chromatograms of Ginsenoside Rg3 (channel I, m/z 783.8→160.8) and internal standard Dioscin (channel II, m/z 867.5→721.5) in liver homogenate determined by LC/MS/MS methods; wherein (A) blank liver homogenates of rats; (B) adding 2 ng/ml Ginsenoside Rg3 and 100 ng/ml internal standard Dioscin to the blank liver homogenates of rats; (C) cerebrospinal fluid sample after administering orally 10 mg/kg Ginsenoside Rg3 to rats (10.8 ng/g).

FIG. 2 shows the chromatograms of the blank sample of the rat cerebrospinal fluid, blank sample having adding Rg3 standard reference substance and internal standard (dioscin) solution and sample after administrating.

The results show that endogenous substances in the tissues do not interfere the determination of ginsenoside Rg3 and the internal standard dioscin.

Preparation of Working Curve

Taking homogenate supernatant 200 μl of rat tissue of the blank control group, and adding the ginsenoside Rg3 reference series solution 100 μl (adding the 100 μl of Rg3 reference solution to the 2000 of supernatant) to prepare tissue samples with the equivalent tissue concentrations of 2, 4, 10, 20, 40, 100, 200 and 400 ng/g. Except for the addition of 100 μl of methanol, operating under the standard of "tissue sample processing" to establish the working curve. Regression calculation is performed with the weighted least squares method by taking the analyte concentration as the abscissa value, and taking the peak area ratio of analyte to the internal standard spectrum as the ordinate value, to obtain a linear regression equation which is the working curve.

According to the working curve, the linear range of the measured concentration of ginsenoside Rg3 is: 2-400 ng/g, with the minimum of 2 ng/g. Working curve: y=0.0014+0.0091x (r=0.9992).

Simultaneously quality control samples (QC samples) of high, medium and low concentrations are made, and two-sample analysis performed on each concentration. The concentration of QC samples is calculated according to the working curve of each analysis batch, and at most 2 out of 6 QC (total of 18 samples) samples with different concentrations are allowed to exceed 15% of the theoretical value (the lowest point at 20%), otherwise this batch data is not accepted.

Sample Measurement of Different Preparations

Operation is carried out under the standard of "tissue sample processing", to prepare a working curve for each analysis batch, and the measured results of the cerebrospinal fluid samples of administered rats are shown in table 8.

Data Processing

Medicine concentration data in the cerebrospinal fluid of each administered rat is given out respectively, and the average value and standard deviation are calculated.

TABLE 8

Content of ginsenoside Rg3 in cerebrospinal fluid of rats during BBB test for different preparations

| Preparations | Characteristics of dosage forms | High dose concentrations (mg/kg) | Content of Rg3 in the cerebrospinal fluid (x ± s, ng/g) |
|---|---|---|---|
| Embodiment 1 | Topical application, different transdermal and solubilization excipients | 10 | 6.8 ± 2.1 |
| Embodiment 2 | Topical application, different transdermal and solubilization excipients | 10 | 8.1 ± 3.2 |
| Embodiment 6 | Emulsion for injection, phosphatide excipients | 6 | 19.5 ± 4.3 |
| Embodiment 7 | Topical application, Radix Ginseng oil BBB promoters | 10 | 30.2 ± 11.1 |
| Embodiment 8 | Topical application, Radix Curcumae oil BBB promoters | 10 | 32.1 ± 13.0 |
| Embodiment 9 | Topical application, Moschus oil BBB promoters | 10 | 35.0 ± 13.9 |
| Embodiment 10 | Topical application, rhizoma chuanqiong oil BBB promoters | 10 | 30.9 ± 13.5 |
| Embodiment 11 | Topical application, Rhizoma Acori Tatarinowii oil BBB promoters | 10 | 30.2 ± 14.0 |
| Embodiment 12 | topical application, borneolum syntheticum BBB promoters | 10 | 20.8 ± 7.8 |
| Embodiment 13 | Topical application, calculus bovis artifactus BBB promoters | 10 | 22.2 ± 7.5 |
| Embodiment 14 | Topical application, styrax BBB promoters | 10 | 23.0 ± 6.9 |
| Embodiment 16 | Emulsion for injection, soybean oil excipients | 6 | 20.0 ± 5.3 |
| Embodiment 17 | Oral emulsion, Radix Ginseng volatile oil BBB promoters | 20 | 26.2 ± 8.2 |
| Embodiment 18 | Oral emulsion, Rhizoma Acori Tatarinowii BBB promoters | 20 | 21.5 ± 6.0 |
| Embodiment 19 | Oral emulsion, tulip oil BBB promoters | 20 | 23.3 ± 4.9 |
| Embodiment 20 | Oral emulsion, rhizoma chuanqiong oil BBB promoters | 20 | 25.6 ± 5.4 |
| Embodiment 21 | Oral emulsion, Moschus oil BBB promoters | 20 | 22.0 ± 6.8 |
| Embodiment 25 | Granules, Rhizoma Chuanxiong oil BBB promoters | 20 | 19.5 ± 7.9 |
| Embodiment 26 | Tablets, Radix Ginseng oil BBB promoters | 20 | 18.0 ± 6.1 |
| Embodiment 27 | Oral solution, rhizoma chuanqiong oil BBB promoters | 20 | 21.8 ± 5.2 |
| Embodiment 28 | Aerosol, Moschus oil BBB promoters | 10 | 36.9 ± 14.6 |
| Embodiment 29 | Naristillae, rhizoma chuanqiong oil BBB promoters | 10 | 45.1 ± 16.4 |

The measurement results in table 8 show that through the medicine concentration of ginsenoside Rg3 measured in the cerebrospinal fluid of rats administered with the different dosage forms (typical) of the ginsenoside Rg3 developed by the present invention, the various dosage forms of the present invention can all penetrate the blood-brain barrier into the encephala to play a therapeutic effect.

The invention claimed is:

1. A ginsenoside Rg3 composition consisting of 20(R)-ginsenoside Rg3 with a purity of 98%, Rhizoma Chuanxiong volatile oil, 60% ethanol, polyethylene glycol 200, glycerol, and water, and the weight or volume ratio of the 20(R)-ginsenoside Rg3 with the purity of 98%, Rhizoma Chuanxiong volatile oil, 60% ethanol, polyethylene glycol 200, and glycerol is 1 g:1 g:10 ml:5 ml:20 g.

2. A method of producing the ginsenoside Rg3 composition of claim 1, comprising the following steps: weighing accurately 1 g of ginsenoside Rg3 with a purity of 98% and 1 g of Rhizoma Chuanxiong oil, adding 10 ml of 60% ethanol, 5 ml of polyethylene glycol 200, and 20 g of glycerol, heating the mixture, stirring to dissolve the mixture, and adding water to obtain the ginsenoside Rg3 composition.

3. A method of treating Alzheimer's disease, comprising a step of administering an effective amount of the ginsenoside Rg3 composition of claim 1 to a patient in need.

* * * * *